United States Patent [19]
Gilbert, Jr.

[11] Patent Number: 4,768,926
[45] Date of Patent: Sep. 6, 1988

[54] REMOTE CONTROL FAN

[76] Inventor: Billy D. Gilbert, Jr., 1106 E. Cruces St., Wilmington, Calif. 90744

[21] Appl. No.: 78,685

[22] Filed: Jul. 27, 1987

[51] Int. Cl.⁴ .............................................. F04B 21/00
[52] U.S. Cl. ...................................... 416/61; 415/118; 416/170 R; 417/572
[58] Field of Search ...................... 417/572; 416/5, 61, 416/247 R, 170 C; 415/121 G, 118; 340/671

[56] References Cited

U.S. PATENT DOCUMENTS

| | | | |
|---|---|---|---|
| 3,371,855 | 3/1968 | Bruns | 415/118 |
| 3,575,527 | 4/1971 | Watanabe | 416/32 |
| 4,087,927 | 5/1978 | Basmajian | 415/118 X |
| 4,479,115 | 10/1984 | Holzhauer | 415/118 X |
| 4,538,973 | 9/1985 | Angott et al. | 417/572 |
| 4,675,663 | 6/1987 | Corwin | 416/61 X |

FOREIGN PATENT DOCUMENTS

| | | | |
|---|---|---|---|
| 818291 | 8/1959 | United Kingdom | 416/61 |
| 913718 | 12/1962 | United Kingdom | 416/247 |

Primary Examiner—Everette A. Powell, Jr.
Attorney, Agent, or Firm—Leon Gilden

[57] ABSTRACT

A portable fan is provided with a remote control assembly to facilitate its use by handicapped persons. The switch on the fan is operated by a radio controlled receiver, and a hand held transmitter is designed to permit a user to select multiple fan speeds and direction of blade rotation. Additionally, the transmitter emits audible beeps so as to allow the use of the remote fan control by blind individuals.

4 Claims, 2 Drawing Sheets

REMOTE CONTROL FAN

BACKGROUND OF THE INVENTION

1. Field of the Invention

The present invention relates to powered ventilation devices, and more particularly pertains to a new and improved fan unit which can be operated by a remote control apparatus.

2. Description of the Prior Art

Remote control technology is quite sophisticated and the use of remote control devices for powering various appliances and other equipment is well known in the prior art. A good example of a sophisticated use of remote control technology is disclosed in U.S. Pat. No. 4,369,543 which issued to Chen et al on Jan. 25, 1983. In this patent, there is disclosed a remote control operation of a vacuum cleaner wherein a user can operate such a cleaner through the use of a small hand held transmitter without virtually any physical exertion on his part. Of course, remote control operation of television sets and the like is also well known in the art, and it can be appreciated that remote control technology is particularly useful to the handicapped and elderly who would otherwise have substantial difficulty in operating certain types of equipment.

The selective multi-functional operation of various equipment is facilitated by the use of the aforementioned hand held transmitters wherein different frequency signals can be delivered to a receiver mounted on a piece of equipment, thus to cause that equipment to perform different selected operations. A typical example of a hand held transmitter for transmitting different frequency signals is disclosed in U.S. Pat. No. 4,218,681 which issued to M. Hormann on Aug. 19, 1980. There has been at least one attempt to develop a remote control system for a fan assembly and in this respect, reference is made to U.S. Pat. No. 4,538,973 which issued to Angott et al on Sept. 3, 1985. The Angott et al device includes a ceiling mounted fan and light assembly which is remotely controlled by radio signals propagated by a remote transmitter with the transmitter having independent controls for the fan and light respectively. The receiver has two channels and is responsive to the transmitter signals in a manner which allows the selection of multiple fan speeds and different levels of light illumination. While being functional for its intended purpose, this remotely controlled fan assembly is not particularly adaptable for use by blind individuals inasmuch as they cannot easily determine the chosen fan speed, nor is any suggestion made for utilizing the remote control technology on a portable fan which would greatly increase its versatility of use. As such, it would appear that there exists a continuing need for an improved remotely controllable fan unit which would be easily used by blind individuals, as well as by others desiring the convenience thereof, and further wherein such remote control could be employed on portable fans. In this respect, the present invention substantially addresses this need.

SUMMARY OF THE INVENTION

In view of the foregoing disadvantages inherent in the known types of remote control assemblies for use with fans now present in the prior art, the present invention provides an improved remote control assembly for use with fans wherein the same is adaptable for operation with a portable fan unit and further wherein an associated transmitter provides both an audible and visual indication of the chosen fan speed and direction of rotation. As such, the general purpose of the present invention, which will be described subsequently in greater detail, is to provide a new and improved remotely controlled fan which has all the advantages of the prior art remotely controlled fans and none of the disadvantages.

To attain this, the present invention relies upon the technology disclosed in U.S. Pat. No. 4,218,681 and in U.S. Pat. No. 4,538,973, as aforediscussed, the disclosures of which are incorporated herein by reference. More particularly, a switch operating receiver is mounted on a portable fan, and an associated hand held transmitter is designed to include parallel electric circuits which provide concurrently actuated and visual signals relating to the chosen fan speed and direction of rotation. When the user transmits a signal relating to a low fan speed, a single audible beep is emitted from the transmitter and a light emitting diode display indicates that a low speed has been chosen. When a medium fan speed is chosen, two audible beeps are heard and the visual display changes accordingly. If a high speed is provided, three audible beeps are provided and the visual indicator again changes. Further, a reverse direction of blade rotation is provided on a separate channel, thus to change the direction of air flow through the fan, and a different audible tone or a greater number of audible beeps can be provided to indicate the newly chosen direction of blade rotation.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out it various ways. Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved remotely controlled fan which has all the advantages of the prior art remotely controlled fans and none of the disadvantages.

It is another object of the present invention to provide a new and improved remotely controlled fan which may be easily and efficiently manufactured and marketed.

It is a further object of the present invention to provide a new and improved remotely controlled fan which is of a durable and reliable construction.

An even further object of the present invention is to provide a new and improved remotely controlled fan which is susceptible of a low cost of manufacture with regard to both materials and labor, and which accordingly is then susceptible of low prices of sale to the consuming public, thereby making such remotely controlled fans economically available to the buying public.

Still yet another object of the present invention is to provide a new and improved remotely controlled fan which provides in the apparatuses and methods of the prior art some of the advantages thereof, while simultaneously overcoming some of the disadvantages normally associated therewith.

Still another object of the present invention is to provide a new and improved remotely controlled fan which is particularly adaptable for use by blind individuals.

Yet another object of the present invention is to provide a new and improved remotely controlled fan which is designed for use on a portable fan.

These together with other objects of the invention along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
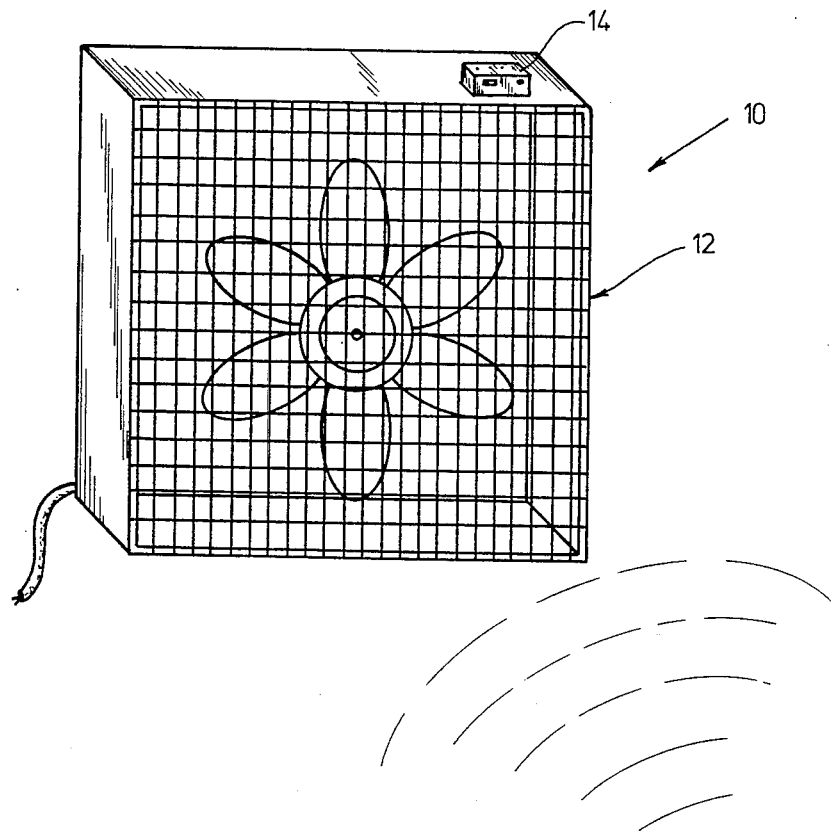
FIG. 1 is a perspective view of the remotely controlled fan and associated transmitter comprising the present invention.
Figure 2:
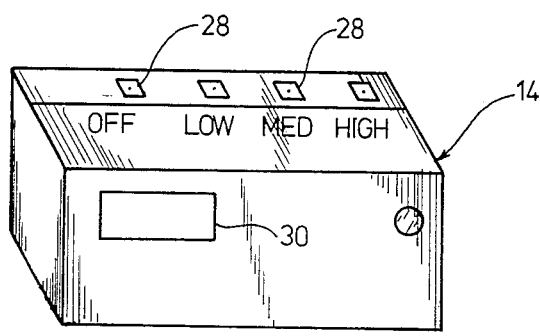
FIG. 2 is a perspective view of the receiver control box mounted on the fan.

With reference now to the drawings, and in particular to FIGS. 1 and 2 thereof, a new and improved remotely controlled portable fan assembly embodying the principles and concepts of the present invention and generally designated by the reference numeral 10 will be described.

More specifically, it will be noted that the remotely controlled fan assembly 10 essentially consists of a portable electrically powered fan 12 to which a receiver control box 14 is operably mounted. The portable fan 12 is capable of a reverse blade rotation operation much in the manner of commercially available ceiling fans, and a separate hand held transmitter 16 of a multi-channel capability is used to control the operation of the fan. As illustrated, the hand held transmitter includes an on-and-off switch 18, a low fan speed switch 20, a medium fan speed switch 22, and a high fan speed switch 24. Additionally, a reverse blade rotation switch 26 is also provided. Inasmuch as each of the switches 20-26 are electrically powered to generate a controlling radio signal, small audible speaker systems are electrically wired in parallel with each of the switches and are operative to give different audible signals to indicate to a user which switch has been actuated. Differences in tone can be employed or a different number of the same audible tone can be used to indicate switch selection.

FIG. 2 of the drawings more particularly illustrates the receiver control unit 14 mounted directly on the fan 12. The receiver control unit 14 may include a plurality of manual control buttons, all of which are generally designated by the reference numeral 28, so as to permit an operation of the fan 12 without a use of the remote control transmitter 16. Regardless of whether the fan 12 is manually operated or operated by means of the remote control transmitter 16, a light emitting diode display 30 is utilized to indicate the selected fan speed. In this respect, the word "LOW" will be displayed when a low fan speed is chosen, the word "MED" will be displayed when a medium fan speed is chosen, and the word "HI" will be displayed in response to a selected high speed of fan rotation. No display will be provided for the direction of blade rotation inasmuch as this can be determined by the user from just noting the direction of air movement.

As to the manner of usage and operation of the present invention, the same should be apparent from the above description. Accordingly, no further discussion relating to the manner of usage and operation will be provided. In summary, it can be appreciated that the present invention is particularly well adapted for use by the handicapped and elderly, and specifically blind individuals since the audible tone arrangement allows a blind person to select a particular fan speed without any difficulty.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A new and improved remotely controlled fan assembly comprising:

portable fan means for circulating air having at lease two speeds of rotation;

remote switching means for remotely selecting one of said at least two fan speeds;

first indicating means for indicating to a user a selected fan speed wherein said first indicating means comprises a visual light emitting diode display fixedly secured to said fan means indicating said selected fan speed; wherein said second indicating means comprises an audible signal representative of said selected fan speed associated with a hand-held transmitter forming a part of said remote switching means.

2. The new and improved remotely controlled fan assembly as described in claim 1, wherein said light emitting diode display is mounted in a receiver control box fixedly secured to said fan means.

3. The new and improved remotely controlled fan assembly as described in claim 1, and further including a fan blade direction of rotation changing means.

4. The new and improved remotely controlled fan assembly as described in claim 3, wherein a first radio channel is utilized in said remote switching means for controlling a selection of said fan speed and a second radio channel is utilized in said remote switching means for controlling fan blade direction of rotation changing means.

* * * * *